United States Patent
Okamoto et al.

(10) Patent No.: US 9,919,992 B2
(45) Date of Patent: Mar. 20, 2018

(54) POLYETHER DIOL AND METHOD FOR PRODUCING THE SAME

(71) Applicant: Mitsubishi Gas Chemical Company, Inc., Chiyoda-ku (JP)

(72) Inventors: Atsushi Okamoto, Niigata (JP); Hideyuki Sato, Niigata (JP); Umi Yokobori, Niigata (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 15/514,982

(22) PCT Filed: Sep. 29, 2015

(86) PCT No.: PCT/JP2015/077452
§ 371 (c)(1),
(2) Date: Mar. 28, 2017

(87) PCT Pub. No.: WO2016/052476
PCT Pub. Date: Apr. 7, 2016

(65) Prior Publication Data
US 2017/0240495 A1    Aug. 24, 2017

(30) Foreign Application Priority Data
Sep. 29, 2014 (JP) .................. 2014-198480

(51) Int. Cl.
*C07C 43/196* (2006.01)
*C07C 41/28* (2006.01)

(52) U.S. Cl.
CPC ............ *C07C 43/196* (2013.01); *C07C 41/28* (2013.01); *C07C 2601/14* (2017.05)

(58) Field of Classification Search
CPC .... C07C 43/196; C07C 41/28; C07C 2101/14
See application file for complete search history.

(56) References Cited

U.S. PATENT DOCUMENTS

| | | |
|---|---|---|
| 2005/0148802 A1 | 7/2005 | Wartini et al. |
| 2006/0115664 A1 | 6/2006 | Dontula et al. |
| 2010/0048940 A1 | 2/2010 | Tulchinsky et al. |
| 2010/0164127 A1 | 7/2010 | Noro |
| 2015/0329454 A1 | 11/2015 | Okamoto et al. |

FOREIGN PATENT DOCUMENTS

| | | |
|---|---|---|
| JP | 7-165655 A | 6/1995 |
| JP | 2005-534726 A | 11/2005 |
| JP | 2012-500849 A | 1/2012 |
| WO | 2008/142931 A1 | 11/2008 |
| WO | 2014/104341 A1 | 7/2014 |

OTHER PUBLICATIONS

International Search Report dated Dec. 1, 2015, in PCT/JP2015/077452, filed Sep. 29, 2015.

*Primary Examiner* — Rosalynd A Keys
(74) *Attorney, Agent, or Firm* — Oblon, McClelland, Maier & Neustadt, L.L.P.

(57) ABSTRACT

A polyether diol compound represented by the following formula (3):

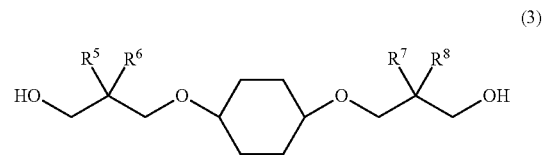

(3)

where $R^5$, $R^6$, $R^7$ and $R^8$, which may be the same as or different from each other, each represent a linear or branched alkyl group having 1 to 6 carbon atoms.

20 Claims, No Drawings

POLYETHER DIOL AND METHOD FOR PRODUCING THE SAME

TECHNICAL FIELD

The present invention relates to a polyether diol and a method for producing the same.

BACKGROUND ART

Various types of polyether diols having a plurality of ether bonds and two hydroxyl groups in combination in a molecule have been synthesized and used industrially for a wide range of products including surfactants, emulsifiers and lubricants. As the polyether diols, diol compounds having a hydroxyl group at both ends of an oxyalkylene chain obtained by ring opening polymerization of ethylene oxide or propylene oxide are known and most generally used.

As a modified polyether diol, a polyether diol having a structure obtained by adding ethylene oxide or propylene oxide to a hydroxyl group(s) of a higher diol is also known. As such a polyether diol, a polyether diol prepared by ring opening addition of a plurality of ethylene oxides or propylene oxides to 2,2-dimethyl-1,3-propanediol (neopentyl glycol) and trimethylolpropane are known (Patent Document 1).

As a higher polyether diol containing a cyclohexane ring, 1,4-bis(2-hydroxy-ethoxy)-cyclohexane is disclosed in Patent Document 2; and 1,4-bis(2-hydroxy-ethoxymethyl)-cyclohexane and 1,3-bis(2-hydroxy-ethoxymethyl)-cyclohexane are disclosed in Patent Document 3.

CITATION LIST

Patent Document

Patent Document 1: National Publication of International Patent Application No. 2005-534726
Patent Document 2: U.S. Patent No. 2006/115664
Patent Document 3: Japanese Patent Application Laid-Open No.2012-500849

SUMMARY OF INVENTION

Technical Problem

Of the polyether diols, a polyether diol having an intramolecular oxyalkylene skeleton derived from ethylene oxide or propylene oxide has high polarity due to the skeleton; in other words, the oxyalkylene skeleton has hydrophilicity. Because of this, such a polyether diol and a polymer derived from such a polyether diol are known to have problems: less solubility to lipophilic polymers and easily hydrolysis by easily absorbing water. Then, it has been desired to develop a highly lipophilic polyether diol composed of a cyclohexane ring structure and a neopentyl glycol structure.

An object of the present invention is to provide a novel polyether diol overcoming the aforementioned problems in the art and a method for efficiently producing the polyether diol.

Solution to Problem

The present inventors have conducted intensive studies on a highly lipophilic polyether diol. As a result, they found that a polyether diol having a specific structure possibly has high lipophilicity and arrived at the present invention.

More specifically, the present invention is as follows.
<1> A polyether diol compound represented by the following formula (3):

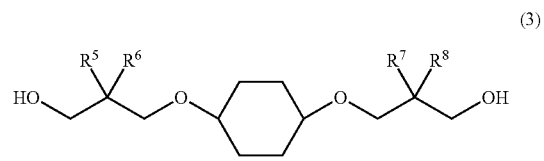

where $R^5$, $R^6$, $R^7$ and $R^8$, which may be the same as or different from each other, each represent a linear or branched alkyl group having 1 to 6 carbon atoms.
<2> The compound according to [1], in which a combination of the $R^5$ and the $R^6$ and a combination of $R^7$ and $R^8$ are the same as each other.
<3> The compound according to [1], in which at least one of the combination of $R^5$ and $R^6$ and the combination of $R^7$ and $R^8$ is a combination of substituent groups selected from the group consisting of a combination of a methyl group and a methyl group, a combination of an ethyl group and an ethyl group, a combination of a methyl group and a normal propyl group, and a combination of an ethyl group and a normal butyl group.
<4> The compound according to [1], in which all of $R^5$, $R^6$, $R^7$ and $R^8$ are a methyl group.
<5> A method for producing a polyether diol, comprising hydrogenation reduction of a compound represented by the following formula (1) in the presence of a hydrogenation catalyst to obtain a polyether diol compound represented by the following formula (2):

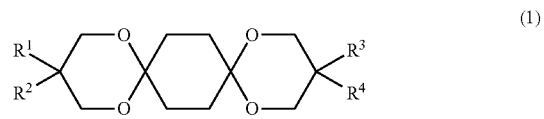

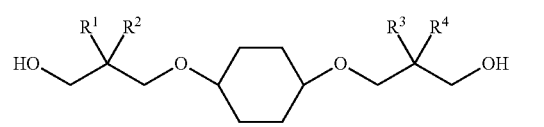

where $R^1$, $R^2$, $R^3$ and $R^4$, which may be the same as or different from each other, each represent a linear or branched alkyl group having 1 to 6 carbon atoms.
<6> The method according to [5], in which a combination of $R^1$ and $R^2$ and a combination of $R^3$ and $R^4$ are the same as each other.
<7> The method according to [5], in which at least one of the combination of $R^1$ and $R^2$ and the combination of $R^3$ and $R^4$ is a combination of substituent groups selected from the group consisting of a combination of a methyl group and a methyl group, a combination of an ethyl group and an ethyl group, a combination of a methyl group and a normal propyl group, and a combination of an ethyl group and a normal butyl group.
<8> The method according to [5], in which all of $R^1$, $R^2$, $R^3$ and $R^4$ are a methyl group.
<9> The method according to any one of <5> to <8>, in which the compound represented by the general formula (1) is subjected to hydrogenation reduction in a reaction solvent containing at least one selected from the group consisting of ether compounds and saturated hydrocarbon compounds.
<10> The method according to any one of <5> to <9>, in which the hydrogenation catalyst is a solid catalyst containing palladium.
<11> The method according to any one of <5> to <10>, in which the hydrogenation catalyst is a solid catalyst containing a zirconium compound.

Advantageous Effects of Invention

According to the present invention, it is possible to obtain a novel polyether diol composed of a cyclohexane ring structure and a neopentyl glycol structure and efficiently produce such a polyether diol.

DESCRIPTION OF EMBODIMENTS

Now, an embodiment of the present invention (hereinafter simply referred to as "the embodiment") will be described. Note that the following embodiment is an example illustrating the present invention and the present invention is not limited to the embodiment alone.
<Polyether Diol>
The polyether diol of the embodiment has one cyclohexane ring structure and two neopentyl glycol structures in a molecule. These structures are connected with ether bonds to form the polyether diol. More specifically, the polyether diol of the embodiment has a structure represented by the following formula (3). The structure will be more specifically described below.

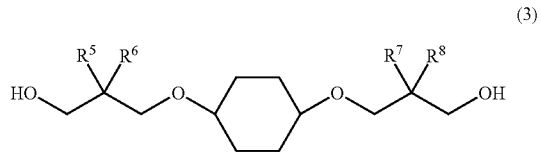

(3)

where $R^5$, $R^6$, $R^7$ and $R^8$, which may be the same as or different from each other, each represent a linear or branched alkyl group having 1 to 6 carbon atoms. A compound represented by formula (3) may have a plurality of geometric isomers. In the embodiment, one or both of the geometric isomers are shown. The production ratio of geometric isomers of a polyether diol represented by formula (3) varies depending upon e.g., the reaction conditions, the type of reaction solvent and the type of catalyst and is not particularly limited. The mixture of geometric isomers of a polyether diol obtained by the production method that will be described later can be directly used as the mixture or separated into individual geometric isomers by a method known in the art and then put in use.

Examples of each of $R^5$, $R^6$, $R^7$ and $R^8$ in the above formula (3) include a methyl group, an ethyl group, an n-propyl group (a normal propyl group), a 1-methylethyl group (an isopropyl group), an n-butyl group (a normal butyl group), a 1-methylpropyl group, a 2-methylpropyl group, a 1,1-dimethylethyl group (a tert-butyl group), a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group (a neopentyl group), a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group and a 1-ethyl-2-methylpropyl group. Of these, $R^5$, $R^6$, $R^7$ and $R^8$ are preferably each independently a methyl group, an ethyl group, an n-propyl group or a 1-methylethyl group (an isopropyl group), an n-butyl group, a 1-methylpropyl group, a 2-methylpropyl group or a 1,1-dimethylethyl group (a tert-butyl group). $R^5$, $R^6$, $R^7$ and $R^8$ are more preferably each independently a methyl group, an ethyl group, a n-propyl group or a n-butyl group.

More specifically, examples of the combination of $R^5$ and $R^6$ and the combination of $R^7$ and $R^8$ each independently include a combination of a methyl group and a methyl group, a combination of a methyl group and an ethyl group, a combination of a methyl group and a propyl group, a combination of a methyl group and a hexyl group, a combination of an ethyl group and an ethyl group and a combination of an ethyl group and a butyl group and a propyl group and a pentyl group. Of these, a combination of a methyl group and a methyl group, a combination of a methyl group and a normal propyl group, a combination of an ethyl group and an ethyl group and a combination of an ethyl group and a normal butyl group are preferable, and a combination of a methyl group and a methyl group is particularly preferable.

Of these, what is a preferable compound in order to particularly simplify a production method is a compound in which the combination of $R^5$ and $R^6$ and the combination of $R^7$ and $R^8$ are the same as each other. Specific examples of each of the combination of $R^5$ and $R^6$ and the combination of $R^7$ and $R^8$ include a combination of a methyl group and a methyl group, a combination of a methyl group and an ethyl group, a combination of a methyl group and a propyl group, a combination of a methyl group and a hexyl group, a combination of an ethyl group and an ethyl group, a combination of an ethyl group and a butyl group, and a combination of a propyl group and a pentyl group. Of these, a combination of a methyl group and a methyl group, a combination of a methyl group and a normal propyl group, a combination of an ethyl group and an ethyl group, a combination of an ethyl group and a normal butyl group are preferable, and a combination of a methyl group and a methyl group is particularly preferable. In this particularly preferable case, all of $R^5$, $R^6$, $R^7$ and $R^8$ are a methyl group.

Of conventional polyether diols, a polyether diol having a structural unit of an oxyalkylene skeleton derived from ethylene oxide or propylene oxide in the molecule has a low chemical stability. Due to the low chemical stability, the polyether diol is oxidized with oxygen and light and deteriorates with time. This is due to the structural unit of an oxyalkylene skeleton contained in the molecule and occurs even in a polyether diol modified by a higher diol. In contrast, the polyether diol of the present invention has not only excellent thermal stability but also excellent oxidation resistance.

The polyether diol of the embodiment can be synthesized by the production method of the embodiment that will be described below. In the production method of the embodiment, a polyether diol represented by the following formula (2) is obtained by hydrogenation reduction of a polycyclic acetal (hereinafter referred to simply as a "polycyclic acetal") represented by the following formula (1) in the presence of a hydrogenation catalyst.

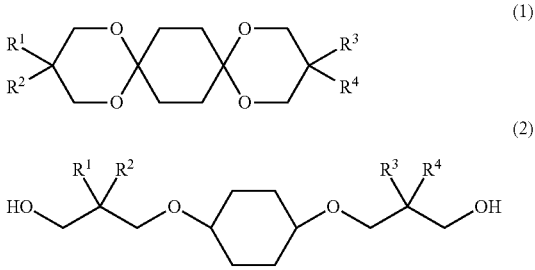

where $R^1$, $R^2$, $R^3$ and $R^4$, which may be the same as or different from each other, each represent a linear or branched alkyl group having 1 to 6 carbon atoms. A compound represented by formula (2) may have a plurality of geometric isomers. In the embodiment, one or both of the geometric isomers are shown. The production ratio of geometric isomers of a polyether diol represented by formula (2) varies depending upon e.g., the reaction conditions, the type of reaction solvent and the type of catalyst and is not particularly limited. The mixture of geometric isomers of a polyether diol obtained can be directly used as the mixture or separated into individual geometric isomers by a method known in the art and then put in use.

Compounds represented by formula (1) and formula (2) may sometimes have a plurality of optical isomers depending upon the combination of alkyl groups represented by $R^1$, $R^2$, $R^3$ and $R^4$.

<Raw-Material Compound>

A compound used as a raw-material in the method for producing a polyether diol of the embodiment (hereinafter also referred to simply as the "production method") is a polycyclic acetal represented by the above formula (1).

The raw-material for synthesis, a production process thereof, and the like to be used in the embodiment are not particularly limited and a material produced by a method known in the art can be used. The simplest and most efficient method for producing a polycyclic acetal is a method comprising cyclodehydration of cyclohexane-1,4-dione and 2,2-disubstituted-1,3-propanediol in the presence of an acid catalyst known in the art. Other than this, a production method based on an acetal exchange reaction between a lower alcohol acetal of cyclohexane-1,4-dione and 2,2-disubstituted-1,3-propanediol may be employed.

In the case of producing a polyacetal by cyclodehydration of cyclohexane-1,4-dione and 2,2-disubstituted-1,3-propanediol in the presence of an acid catalyst, the 2,2-disubstituted-1,3-propanediol to be employed is, for example, selected from the following group A.

[Group A]
2,2-dimethyl-1,3-propanediol,
2,2-diethyl-1,3-propanediol,
2-methyl-2-ethyl-1,3-propanediol,
2-methyl-2-propyl-1,3-propanediol,
2-methyl-2-butyl-1,3-propanediol,
2-ethyl-2-butyl-1,3-propanediol,
2-propyl-2-pentyl-1,3-propanediol,
2-methyl-2-hexyl-1,3-propanediol.

The substituent groups bonded to the carbon atom at position 2 of 1,3-propanediol correspond to the groups represented by $R^1$, $R^2$, $R^3$ and $R^4$ in the above formula (1).

Examples of $R^1$, $R^2$, $R^3$ and $R^4$ in the above general formula (1) each independently include a methyl group, an ethyl group, a n-propyl group, a 1-methylethyl group (isopropyl group), a n-butyl group, a 1-methylpropyl group, a 2-methylpropyl group, a 1,1-dimethylethyl group (tert-butyl group), a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group (neopentyl group), a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, and a 1-ethyl-2-methylpropyl group. Of these, $R^1$, $R^2$, $R^3$ and $R^4$ is each independently preferably a methyl group, an ethyl group, a n-propyl group or a 1-methylethyl group (isopropyl group), a n-butyl group, a 1-methylpropyl group, a 2-methylpropyl group, a 1,1-dimethylethyl group (tert-butyl group). $R^1$, $R^2$, $R^3$ and $R^4$ are more preferably each independently a methyl group, an ethyl group, a n-propyl group or a n-butyl group.

The polycyclic acetal to be used in the embodiment, which is not particularly limited as long as it is a compound represented by the above formula (1), may be a single (single type) compound or a mixture of two or more compounds represented by formula (1) different in combination of alkyl groups represented by $R^1$, $R^2$, $R^3$ and $R^4$. In the case of the mixture (of two or more compounds), the mixing ratio of the compounds is not particularly limited. In a point of view of separation and recovery of the polyether diol to be produced, using a single polycyclic acetal is the simplest and preferable way.

The present inventors investigated on other isomers of cyclohexanedione as a starting material for a polycyclic acetal. As a diol component serving as a reaction partner, 2,2-dimethyl-1,3-propanediol was used and paratoluenesulfonic acid or Nafion (strong acidic ion exchange resin) was used as an acid catalyst. As a result, when cyclohexane-1,4-dione of the embodiment was used, a desired bis-acetal compound was obtained almost in a stoichiometry amount. In contrast, when cyclohexane-1,3-dione was used, a large amount of a high boiling-point product, presumably a condensation product between cyclohexane-1,3-dione compounds, was by-produced, with the result that the yield of a desired bis-acetal compound drastically decreased. When cyclohexane-1,2-dione was used, only a small amount of a desired bis-acetal compound was obtained probably due to steric hindrance. From this, it is preferable to use a polycyclic acetal represented by the above formula (1) for industrially easily attaining high-yield production.

<Hydrogenation Catalyst>

I. Specific Metal Component

Examples of the active component of the hydrogenation catalyst to be used in the embodiment include a metal element (hereinafter referred to as a " specific metal component") having a catalytic hydrogenation property. Examples of the specific metal component include nickel, cobalt, iron, ruthenium, rhodium, palladium, platinum, iridium, copper, silver, molybdenum, tungsten, chromium and rhenium. As long as the specific metal component exhibits a hydrogenation property, the specific metal component may be present in a metal state or in a cationic state. Of them, the specific metal component is preferably present in a metal state, because the hydrogenation property is generally stronger in a metal state and stable under a reduction atmosphere. Specific metal components may be used singly or in combination (of two or more) in a state where the metal components are contained in a solid catalyst. When the two or more specific metal components are used, the combination, mixing ratio or form of the specific metal components is not particularly limited and the specific metal components may be used as a mixture thereof or in the form of an alloy or an intermetallic compound. In the embodiment, the hydrogenation catalyst is preferably a solid catalyst containing at least one selected from the group consisting of palladium, platinum, nickel and copper, and particularly preferably a solid catalyst containing palladium.

Raw-materials of the specific metal components are not particularly limited. Raw-materials used for preparing a catalyst by a method known in the art can be employed. Examples of such raw-materials include a hydroxide, an oxide, a fluoride, a chloride, a bromide, an iodide, a sulfate, a nitrate, an acetate, an ammine complex and a carbonyl complex of each of the metal elements. These are used singly or in combination (two or more).

In the hydrogenation catalyst of the embodiment, the specific metal components may be used singly or in combination with a having no catalytic hydrogenation property, as the metal component. Examples of the catalyst using a single specific metal component include a catalyst consisting of fine powder of a specific metal component such as palladium black and platinum black. Examples of the catalyst consisting of a specific metal component and a metal having no catalytic hydrogenation property in combination include a sponge catalyst, which is prepared by forming an alloy from a specific metal component, aluminum and a small amount of additives, and allowing a whole or part of aluminum to leach out.

II. Specific Addition Component

In order to further improve e.g., the activity, selectivity and physical properties of a catalyst, at least one element selected from the group consisting of alkali metal elements, such as lithium, sodium, potassium, rubidium and cesium; alkaline-earth metal elements, such as magnesium, calcium, strontium and barium; halogen elements, such as fluoride, chlorine, bromine and iodine; and supplemental addition elements, such as mercury, lead, bismuth, tin, tellurium and antimony (hereinafter referred to as a specific addition component) may be added to a catalyst together with a specific metal component as mentioned above.

Raw-materials for these specific addition components are not particularly limited. Raw-materials used in preparing a catalyst by a method known in the art can be employed. Examples of the raw-materials include a hydroxide, an oxide, a fluoride, a chloride, a bromide, an iodide, a sulfate, a nitrate, an acetate and an ammine complex of each of the metal elements. These are used singly or in combination (of two or more). A method for adding a specific addition component or a ratio of a specific addition component to a specific metal component is not particularly limited.

III. Specific Non-Metal Component

In the hydrogenation catalyst of the embodiment, a non-metal substance may be used in combination with a specific metal component. Examples of the non-metal substance include an elementary substance, a carbide, a nitride, an oxide, a hydroxide, a sulfate, a carbonate and a phosphate (hereinafter, the non-metal substance is referred to as a "specific non-metal component"). Specific examples thereof include graphite, diamond, activated carbon, silicon carbide, silicon nitride, aluminum nitride, boron nitride, boron oxide, aluminum oxide (alumina), silicon oxide (silica), titanium oxide, zirconium oxide, hafnium oxide, lanthanum oxide, cerium oxide, yttrium oxide, niobium oxide, magnesium silicate, calcium silicate, magnesium aluminate, calcium aluminate, zinc oxide, chromic oxide, aluminosilicate, alum inosilicophosphate, alum inophosphate, borophosphate, magnesium phosphate, calcium phosphate, strontium phosphate, apatite hydroxide (calcium hydroxyphosphate), apatite chloride, apatite fluoride, calcium sulfate, barium sulfate and barium carbonate. The specific non-metal components are used singly or in combination (of two or more). When the specific non-metal components are used in combination (of two or more), the combination, mixing ratio or form of the specific non-metal components is not particularly limited and the specific non-metal components may be used as a mixture thereof or in the form of a composite compound or a double salt.

In view of industrial use, a specific non-metal component, which can be obtained simply at low cost, is preferable. As such a specific non-metal component, a zirconium compound, an aluminum compound and an apatite compound are preferable and a zirconium compound and an apatite compound (such as calcium hydroxyphosphate) are more preferable. Of them, zirconium oxide is particularly preferable. Specific non-metal components, which are wholly or partially modified or ion-exchanged with the aforementioned specific addition components, can be also used.

As the specific non-metal component, for example, a carbide, a nitride and an oxide of the specific metal component can be used. However, if these are exposed to a hydrogenation reduction atmosphere, they are partly reduced up to metals. In this case, a part of them is used as a specific metal component and the remaining part is used as a non-metal component. Examples of such a case include oxides such as nickel oxide, iron oxide, cobalt oxide, molybdenum oxide, tungstic oxide and chromic oxide.

IV. Hydrogenation Catalyst

As the hydrogenation catalyst of the embodiment, a specific metal component may be used singly or may be used in combination with a specific non-metal component; and, as the case, a specific addition component may be contained in addition to these. The method for producing a hydrogen catalyst of the embodiment is not particularly limited and a method known in the art can be used. Examples thereof include a method (impregnation method) in which the specific non-metal component is impregnated with a raw-material compound for a specific metal component; a method (co-precipitation method) in which both a raw-material compound for a specific metal component and a raw-material compound for a specific non-metal component are dissolved in a suitable solvent and simultaneously precipitated with e.g., an alkali compound; a method (kneading method) in which a raw-material compound for a specific metal component and a specific non-metal component are homogeneously mixed in a suitable ratio.

Depending on the composition of the hydrogenation catalyst or the catalyst preparation method, a specific metal component is prepared in a cation state and then reduced into a metal. As the reduction method and reducing agent to be used herein, those known in the art can be used, but not particularly limited to those. Examples of the reducing agent include reducing inorganic gases such as hydrogen gas, carbon monoxide gas, ammonia, hydrazine, phosphine and silane; a lower oxygen-containing compounds such as methanol, formaldehyde and formic acid; and hydrides such as sodium borohydride and lithium aluminum hydride. A specific metal component is converted into a metal by reducing a specific metal component of a cation state in a gas phase or a liquid phase in the presence of the reducing agent as mentioned above. The conditions for the reduction can be set appropriately depending on the types and amounts of the specific metal component and reducing agent. The reduction treatment may be carried out by using a catalyst reduction apparatus separately before the hydrogenation reaction in the production method of the embodiment, or may be carried out before the initiation of the hydrogenation reaction or simultaneously with the reaction in the reactor to be used in the production method of the embodiment.

The metal content or shape of the hydrogenation catalyst of the embodiment is not particularly limited. The hydrogenation catalyst may be a powder form or a molded form. In the case of a molded hydrogenation catalyst, the shape of the molded catalyst or a method for molding the catalyst is not particularly limited. For example, a spherical form, a tablet form, extrusion form, and crashed form of them into a suitable size may be appropriately selected and used.

A particularly preferable specific metal component is palladium and a catalyst using this will be more specifically described below. When a specific metal component is palladium, in consideration that palladium is a noble metal, it is economically desired to use palladium in a small amount and effectively. Because of this, it is preferable that palladium is preferably used by dispersing it on a catalyst carrier.

As a palladium compound serving as a raw-material for palladium, a palladium compound soluble in water or an organic solvent is suitable. Examples of such a palladium compound include palladium chloride, a tetrachloropalladium salt, a tetraamminepalladium salt, palladium nitrate and palladium acetate. Of them, palladium chloride is preferable since it has industrial availability due to high solubility to water or an organic solvent. Palladium chloride can be used by dissolving it in e.g., an aqueous solution of sodium chloride, diluted hydrochloric acid or ammonia water.

Palladium or a palladium compound is fixed on a catalyst carrier, for example, by adding a solution of a palladium compound to a catalyst carrier or by soaking a catalyst carrier in a solution of a palladium compound. Examples of an immobilization method generally used include adsorption to a carrier, crystallization by evaporation of a solvent and precipitation-deposition using a reducing substance and/or a basic substance reacting with a palladium compound. A suitable method is appropriately used. The content of palladium in the hydrogenation catalyst prepared by the method as mentioned above is preferably 0.01 to 20% by mass, more preferably 0.1 to 10% by mass and further preferably 0.5 to 5% by mass in terms of metal palladium based on the total amount of the hydrogenation catalyst. When the content of palladium is 0.01 wt % or more, a more sufficient hydrogenation rate can be obtained and the conversion of a polycyclic acetal further increases. In contrast, when the content of palladium is 20 wt % or less, the dispersion efficiency of palladium in the hydrogenation catalyst further increases, with the result that palladium can be more effectively used.

Depending on the palladium compound or the catalyst preparation method, palladium may be fixed on a carrier not in a metal state but in a cation state. In this case, the palladium cation (for example, present in a state of a palladium compound) immobilized can be used after it is reduced into a metal palladium. As a reduction method and reducing agent for this, those known in the art can be employed but not particularly limited to those. Examples of the reducing agent include reducing inorganic gases such as hydrogen gas, carbon monoxide gas, ammonia and hydrazine; lower oxygen-containing compounds such as methanol, formaldehyde and formic acid; hydrocarbon compounds such as ethylene, propylene, benzene and toluene; and hydrides such as sodium borohydride and lithium aluminum hydride. A palladium cation can be easily reduced into a metal palladium by contacting the palladium cation with a reducing agent in a gas phase or a liquid phase. The condition of the reducing treatment can be suitably set depending upon the type and amount of the reducing agent. The reduction treatment may be carried out by using a catalyst reduction apparatus separately before the hydrogenation reaction in the production method of the embodiment, or may be carried out before the initiation of the hydrogenation reaction or simultaneously with the reaction in the reactor to be used in the production method of the embodiment.

As a specific non-metal component to be used together with a specific metal component of the present invention, one kind of the preferable compound is zirconium compound. A hydrogenation catalyst containing a zirconium compound will be more specifically described below. The zirconium compound to be used in the embodiment consists of only one or a combination of two or more kinds selected from the group consisting of zirconium oxide, zirconium hydroxide, zirconium carbonate, an alkaline earth zirconates, a rare earth zirconates and zircon.

A particularly preferable zirconium compound is zirconium oxide and a process for producing zirconium oxide is not particularly limited. For example, in a general method known in the art, an aqueous solution of a soluble zirconium salt is decomposed with a basic substance to obtain zirconium hydroxide or zirconium carbonate, which is then, for example, thermally decomposed to prepare zirconium oxide. The raw-material for a zirconium compound used herein is not limited and includes zirconium oxychloride, zirconium oxynitrate, zirconium chloride, zirconium sulfate, zirconium tetra-alkoxide, zirconium acetate and zirconium acetylacetonato. These are used singly or in combination (two or more). Examples of the basic substance to be used for decomposition include ammonia, alkylamines, ammonium carbonate, ammonium hydrogen carbonate, sodium hydroxide, sodium carbonate, sodium hydrogen carbonate, potassium hydroxide, potassium carbonate, potassium hydrogen carbonate, magnesium hydroxide, calcium hydroxide, lanthanum hydroxide, yttrium hydroxide and cerium hydroxide. These are used singly or in combination (two or more).

When zirconium oxide is used as a specific non-metal component, the physical properties or shape thereof is not particularly limited. Also, the purity of zirconium oxide is not particularly limited and a commercially available product having a purity suitable from general use to a high purity can be appropriately used.

When a specific non-metal component such as a zirconium compound is used as a catalyst carrier, e.g., the shape of carriers formed of these compounds, physical properties such as a particle diameter and porosity or a method for supporting a metal component is not particularly limited. The shape, physical properties of the carrier and supporting method to a carrier suitable for the reaction system and conditions can be appropriately selected and put in use. When these compounds are used as catalyst carrier particles, the BET specific surface areas of the particles are not particularly limited. Carrier particles generally having a specific surface area of about 0.1 to 400 $m^2/g$ can be used, for example. The BET specific surface area is preferably 1 to 300 $m^2/g$ and more preferably 10 to 200 $m^2/g$.

<Hydrogenation Reduction Reaction>

The hydrogenation reduction of the embodiment may be performed by using only a polycyclic acetal as a raw-material without reaction solvent or may be performed with reaction solvent. When a reaction solvent is used, the type and concentration of the solvent are not particularly limited as long as the solvent is inert in hydrogenation reduction. Note that when the reaction solvent, which more strongly interacts with a specific metal component of a hydrogenation catalyst than a polycyclic acetal, is used, the reaction rate extremely decreases or the reaction is terminated in some cases. In view of this, it is preferable that a compound containing, for example, phosphorus, nitrogen and/or sulfur is not used as a reaction solvent. Such a solvent may be used in an extremely small amount that produces no significant influence on the reaction rate. Examples of the reaction solvent preferably used include a saturated hydrocarbon compound, an ester compound and an ether compound. These are used singly or in combination (two or more).

Examples of the reaction solvent include saturated hydrocarbons such as n-pentane, iso-pentane, n-hexane, iso-hexane, 2,2-dimethyl-butane, n-heptane, iso-heptane, 2,2,4-trimethylpentane, n-octane, iso-octane, n-nonane and iso-nonane and their isomers; n-decane, n-pentadecane, cyclohexane, methylcyclohexane, dim ethylcyclohexane and isomers thereof; and decalin; ester compounds such as methyl acetate, ethyl acetate, butyl acetate, methyl propionate, methyl n-butyrate, ethyl n-butyrate, butyl n-butyrate, methyl i-butyrate, cyclohexyl n-butyrate, cyclohexyl i-butyrate and methyl valerate and isomers of these ester compounds; ether compounds such as dimethyl ether, diethyl ether, di-n-propyl ether, di-iso-propyl ether, di n-butyl ether, di-iso-butyl ether, di-sec-butyl ether, methyl propyl ether, ethyl propyl ether, methyl butyl ether, methyl pentyl ether, ethyl butyl ether, propyl butyl ether, methyl cyclopentyl ether, methyl cyclohexyl ether, ethyl cyclopentyl ether, ethyl cyclohexyl ether, propyl cyclopentyl ether, propyl cyclohexyl ether, butyl cyclopentyl ether, butyl cyclohexyl ether, ethylene glycol dimethyl ether, ethylene glycol diethyl ether, propylene glycol dimethyl ether, propylene glycol diethyl ether, diethylene glycol dimethyl ether, diethylene glycol diethyl ether, triethylene glycol dimethyl ether, triethylene glycol diethyl ether, tetrahydrofuran, methyl tetrahydrofuran, tetrahydropyran, methyl tetrahydropyran, 1,4-dioxane and dimethyl-1,4-dioxane and isomers of these ether compounds. Note that the saturated hydrocarbon compound serving as the reaction solvent include a linear, branched and cyclic alkanes.

Of these, at least one selected from the group consisting of n-pentane, iso-pentane, n-hexane, iso-hexane, 2,2-dimethyl-butane, n-heptane, iso-heptane, dimethyl ether, diethyl ether, di-n-propyl ether, di-iso-propyl ether, di-n-butyl ether, di-iso-butyl ether, di-sec-butyl ether, methyl propyl ether, tetrahydrofuran, methyltetrahydrofuran, tetrahydropyrane, methyltetrahydropyrane and 1,4-dioxane is preferable. At least one selected from the group consisting of di-iso-propyl ether, 1,4-dioxane and n-hexane is more preferable.

The reaction system of the hydrogenation reduction in the embodiment is constituted of a polycyclic acetal or a liquid phase containing a polycyclic acetal and a reaction solvent, a gas phase of hydrogen gas and a solid phase of the hydrogenation catalyst. The reaction system is not particularly limited as long as these are present together in the reaction system. As the type of reactor used in hydrogenation reaction of the embodiment, a type of reactors known in the art such as a tube, a vessel and a boiler can be used. As a method for supplying a raw-material composition, a continuous flow system or a batch system may be used. A hydrogenation catalyst may be used in a system using a fixed bed, a fluidized bed and a suspension bed known in the art and the system is not particularly limited. In the case where a continuous flow system with a fixed bed are employed, the reaction can be performed under trickle flow condition or bubble flow condition. The raw-material liquid may be fed downwardly (along gravity direction) or upwardly (opposite to gravity direction). The raw-material gas may be fed in parallel or countercurrently to supply of the raw-material liquid.

The reaction temperature in the hydrogenation reduction of the embodiment is preferably 50 to 350° C., more preferably 100 to 300° C. and further preferably 150 to 280° C. When the reaction temperature is 50° C. or more, a higher hydrogenation rate is easily obtained. When the reaction temperature is 350° C. or less, a side reaction accompanying decomposition of a raw material can be further suppressed and the yield of a desired product is successfully increased.

The reaction pressure in the hydrogenation reduction of the embodiment is preferably 0.1 to 30 MPa and more preferably 2 to 15 MPa. When the reaction pressure is 0.1 MPa or more, a higher hydrogenation rate is easily obtained and the conversion of the polycyclic acetal tends to be improved. When the reaction pressure is 30 MPa or less, cost for reaction equipment can be suppressed to a lower level. This is economically tends to be preferable.

When a raw material composition is supplied by a continuous flow system, LHSV (liquid hourly space velocity) of the raw material relative to a catalyst in the hydrogenation reduction of the embodiment is preferably 0.01 to 10 $h^{-1}$ and more preferably 0.05 to 1.0 $h^{-1}$. When the LHSV is the above lower limit or more, hydrogenation reduction of a polycyclic acetal can be more accelerated. In contrast, when the LHSV is the above upper limit or less, the raw material conversion per one path can be improved and then the production process can be simplified.

The hydrogen gas to be used for hydrogenation reduction of the embodiment is not necessary to be particularly highly purified and may be satisfactory when it has quality usually used for an industrial hydrogenation reaction. Since the hydrogenation reaction is accelerated depending on hydrogen partial pressure, the higher the purity of the hydrogen gas to be used, the more preferable, however, hydrogen gas may be mixed with an inert gas in a reaction such as helium, argon, nitrogen and methane. The ratio of hydrogen gas to a polycyclic acetal in the reaction system, which is expressed by the molar ratio of supplied hydrogen gas to the polycyclic acetal when the reaction is performed in the batch system and by the molar ratio of hydrogen gas supply speed to the polycyclic acetal supply speed (means the molar ratio of hydrogen gas to be supplied per unit time) if the reaction is performed in the continuous feeding system, is preferably 0.1 to 300 and more preferably 0.5 to 100. If the molar ratio or supply-speed ratio of hydrogen gas in terms of mole is 0.1 or more, the hydrogenation reaction tends to be more accelerated. In contrast, if the molar ratio or supply-speed ratio of hydrogen gas in terms of mole is 300 or less, the cost of equipment for recycling excessive hydrogen gas tends to be successively suppressed to a lower level.

<Reaction Intermediate>

The present inventors investigated the reaction for obtaining a polyether diol by hydrogenation reduction of a polycyclic acetal. During the investigation process, they found that when a reaction of hydrogenation reduction proceeds at a sufficient reaction rate, two acetal rings are almost simultaneously reduced by hydrogenation to provide a desired polyether diol. In contrast, when the reaction rate is low, for example, in the case of a reaction is carried out at a low temperature, it was found that a mono-ether mono-alcohol compound (hereinafter referred to as "intermediate") having only one of the acetal rings reduced is present in the product.

The present inventors continued the reaction in the same conditions, for example, by extending the reaction time. As a result, they found that the intermediate is reduced and converted into a desired polyether diol and the residual amount of intermediate becomes a trace level. The result suggests that the intermediate can also serve as a raw material for the polyether diol of the embodiment. More specifically, for example, in the case where the intermediate is produced in a relative large amount, when the intermediate is recovered by a method known in the art and then the intermediate alone or a mixture of the intermediate and another polycyclic acetal is subjected to the hydrogenation reduction according to the embodiment, the intermediate can be converted into a polyether diol.

Note that, a method for producing an ether monoalcohol containing a cyclohexane ring by hydrogenation reduction of a cyclic acetal having one cyclohexane ring and one 1,3-dioxane ring bonded to the cyclohexane ring, in the presence of a hydrogenation catalyst, is known in the art. For example, the following production methods are disclosed.

German Patent No. 1196174 (Example 12) discloses a method of producing hydroxybutyl cyclohexyl ether by hydrogenation reduction of 2-methyl-1,5-dioxa-spiro[5.5] undecane in the presence of a copper chromium catalyst.

Japanese Patent No. 3249667 (Example 3) discloses a method of producing 2,2-diethyl-3-(3,3,5-trimethylcyclohexyloxy)-1-propanol by hydrogenation reduction of 3,3-diethyl-8,8,10-trimethyl-1,5-dioxa-spiro[5.5]undecane in the presence of a 5% palladium on carbon catalyst.

Compared to these methods, in the method of the embodiment, the number of 1,3-dioxane rings present in a molecule of a polycyclic acetal used as a raw material is two, which is larger by one than that of the compounds disclosed in German Patent No. 1196174 and Japanese Patent No. 3249667.

In addition, what is produced herein is a polyether diol having two hydroxyl groups. The number of hydroxyl groups is larger by one compared to the compounds disclosed in German Patent No. 1196174 and Japanese Patent No. 3249667. Because of this, in the production method of the embodiment, side reactions such as a hydrogenolysis reaction of an acetal at a non-target site, a hydrogenolysis reaction of a hydroxyl group and a polymerization reaction by the acetal exchange reaction between an acetal and a hydroxyl group, tend to extremely easily occur. Nevertheless, it is surprising that a desired polyether diol can be obtained with a high selectivity.

According to the embodiment, a polyether diol can be efficiently produced by hydrogenation reduction of the polycyclic acetal mentioned above in the presence of a hydrogenation catalyst.

EXAMPLES

Now, the production method of the present invention will be more specifically described by way of Examples and Comparative Examples. The present invention is not limited to the following Examples as long as it falls within the scope of the invention.

The results of a hydrogenation reduction reaction were evaluated by conversion and selectivity calculated in accordance with the following expressions, based on the individual mole numbers of the raw material supplied, the raw material in a reaction solution and the resultant polyether diol, obtained by gas chromatography.

Conversion(%) of raw material (polycyclic acetal)
=100×[1−(mole number of raw material remaining in reaction solution)/(mole number of raw material supplied)]

Selectivity(%) of resultant polyether diol=100×(mole number of desired polyether diol)/[(mole number of raw material supplied)−(mole number of raw material remaining in reaction solution)]

However, when geometric isomers are present in a raw-material polycyclic acetal and the resultant polyether diol, the values of the isomers were added and calculated.

Analysis by gas chromatography was made by use of the following apparatus.

Apparatus: GC-2010 (product name, manufactured by Shimadzu Corporation)

Column: DB-1 (product name, manufactured by Agilent Technologies)

For isolating the product by a mean including chromatography, the following method and materials were used.

First, a mixture of the geometric isomers of a polyether diol produced was reacted with a solution mixture of an acetic anhydride-pyridine to acetylate individual geometric isomers. The acetylated polyether diol geometric isomers were separated by using the following column filler and developing solvent, deacetylated by the reaction with a methanol-potassium carbonate and isolated as polyether diols.

Filler: "Wakogel C-200" (trade name), manufactured by Wako Pure Chemical Industries Ltd.

Developing solvent: Ethyl acetate—toluene

The individual geometric isomers (of the product) isolated were identified by $^1$H-NMR measurement and $^{13}$C-NMR measurement. The measurement conditions are shown below:

Apparatus: ECA500 (product name, manufactured by JEOL Ltd.)

$^1$H-NMR

Nuclide: $^1$H

Measurement frequency: 500 MHz

Measurement sample: 5% $CD_3OD$ solution $^{13}$C-NMR

Nuclide: $^{13}$C

Measurement frequency: 125 MHz

Measurement sample: 5% $CD_3OD$ solution

A raw-material for a reaction, a polycyclic acetal, represented by the above formula (1), was prepared by the following method.

Raw-Material Preparation Example 1

Preparation of 3,3,12,12-tetramethyl-1,5,10,14-tetraoxadispiro[5.2. 5.2]hexadecane 2,2-dimethylpropane-1,3-diol (a reagent, manufactured by Wako Pure Chemical Industries Ltd.) (186.0 g), cyclohexane-1,4-dione (a reagent, manufactured by Tokyo Kasei Kogyo Co., Ltd.) (100.1 g), benzene (587 g) and granular Nafion (trade name,"NR-50", manufactured by Sigma-Aldrich Corporation) (4.5 g) were placed in a 2-L round-bottom flask. While water generated under normal pressure was azeotropically distilled together with benzene and removed out of the system by use of Dean-Stark trap, a reaction was performed until distillation of water stopped. After the residue was filtered, the filtrate was concentrated and cooled to recrystallize. In this manner, 3,3,12,12-tetramethyl-1,5,10,14-tetraoxadispiro[5.2.5.2]hexadecane (hereinafter referred to as "compound A") (215.7 g) was isolated. The scheme of the synthesis reaction is shown below.

Synthetic Reaction of Polycyclic Acetal according to Raw-Material Preparation Example 1

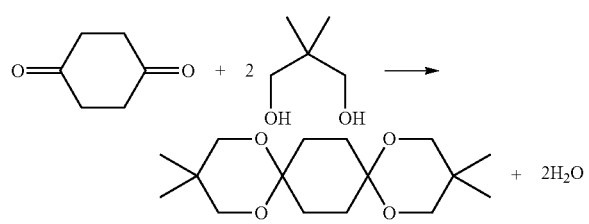

Raw-Material Preparation Example 2

Preparation of 3,3,12,12-tetraethyl-1,5,10,14-tetraoxadispiro[5.2.5.2]hexadecane 3,3,12,12-Tetraethyl-1,5,10,14-tetraoxadispiro[5.2.5.2]hexadecane (hereinafter referred to as "compound B") (109.8 g) was isolated in the same manner as in Raw-Material Preparation Example 1 except that 2,2-diethylpropane-1,3-diol (a reagent, manufactured by Tokyo Kasei Kogyo Co., Ltd.) (101.4 g), cyclohexane-1,4-dione (a reagent, manufactured by Tokyo Kasei Kogyo Co., Ltd.) (42.8 g), benzene (445 g) and granular Nafion (trade name, "NR-50", manufactured by Sigma-Aldrich Corporation) (2.4 g) were placed in a 2-L round-bottom flask. The scheme of the synthesis reaction is shown below.

Synthetic Reaction of Polycyclic Acetal according to Raw-Material Preparation Example 2

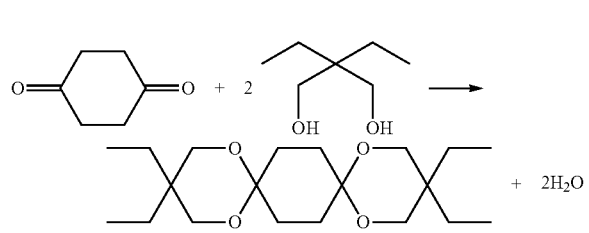

Raw-Material Preparation Example 3

Preparation of 3,12-dimethyl-3,12-dipropyl-1,5,10,14-tetraoxadispiro[5.2.5.2]hexadecane 3,12-Dimethyl-3,12-dipropyl-1,5,10,14-tetraoxadispiro[5.2.5.2]hexadecane (hereinafter referred to as "compound C") (236.2 g) was isolated in the same manner as in Raw-Material Preparation Example 1 except that 2-methyl-2-propylpropane-1,3-diol (a reagent, manufactured by Tokyo Kasei Kogyo Co., Ltd.) (221.6 g), cyclohexane-1,4-dione (a reagent, manufactured by Tokyo Kasei Kogyo Co., Ltd.) (93.9 g), benzene (485 g) and granular Nafion (trade name,"NR-50", manufactured by Sigma-Aldrich Corporation) (4.7 g) were placed in a 2-L round-bottom flask. The scheme of the synthesis reaction is shown below.

Synthetic Reaction of Polycyclic Acetal according to Raw-Material Preparation Example 3

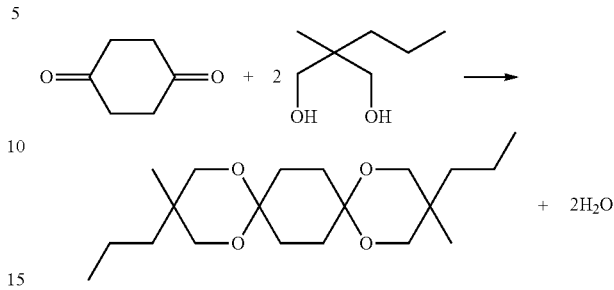

Raw-Material Preparation Example 4

Preparation of 3,12-dibutyl-3,12-diethyl-1,5,10,14-tetraoxadispiro[5.2.5.2]hexadecane 3,12-Dibutyl-3,12-diethyl-1,5,10,14-tetraoxadispiro[5.2.5.2]hexadecane (hereinafter referred to as "compound D") (191.3 g) was isolated in the same manner as in Raw-Material Preparation Example 1 except that 2-butyl-2-ethylpropane-1,3-diol (a reagent, manufactured by Tokyo Kasei Kogyo Co., Ltd.) (178.0 g), cyclohexane-1,4-dione (a reagent, manufactured by Tokyo Kasei Kogyo Co., Ltd.) (62.4 g), benzene (468 g) and granular Nafion (trade name, "NR-50", manufactured by Sigma-Aldrich Corporation) (4.3 g) were placed in a 2-L round-bottom flask. The scheme of the synthesis reaction is shown below.

Synthetic Reaction of Polycyclic Acetal according to Raw-Material Preparation Example 4

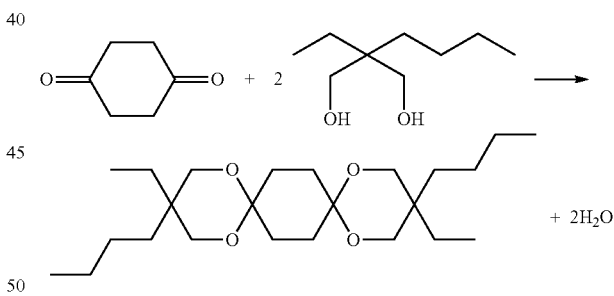

Raw-Material Preparation Reference Example 1

Preparation of 1,5,10,14-tetraoxadispiro[5.2.5.2]hexadecane 1,5,10,14-Tetraoxadispiro[5.2.5.2]hexadecane (hereinafter referred to as "compound E") (28.0 g) was isolated in the same manner as in Raw-Material Preparation Example 1 except that propane-1,3-diol (a reagent, manufactured by Wako Pure Chemical Industries Ltd.) (24.5 g), cyclohexane-1,4-dione (a reagent, manufactured by Tokyo Kasei Kogyo Co., Ltd.) (17.1 g), benzene (165 g) and granular Nafion (trade name,"NR-50", manufactured by Sigma-Aldrich Corporation) (2.5 g) were placed in a 1-L round-bottom flask. The scheme of the synthesis reaction is shown below.

Synthetic Reaction of Polycyclic Acetal according to Raw-Material Preparation Reference Example 1

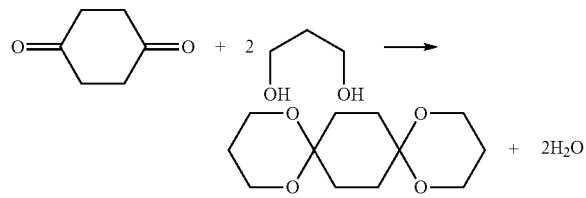

Carrier Preparation Example 1

Zirconium oxide used as a carrier for a metal component was prepared by the following method.

To an aqueous zirconium oxynitrate solution (505 g) of 25% by mass in concentration in terms of the zirconium oxide ($ZrO_2$), 28% ammonia water (15.5 g) was added dropwise while stirring to obtain a white precipitate. The white precipitate was filtered and washed with ion-exchange water, dried at 110° C. for 10 hours to obtain hydrous zirconium oxide. The hydrous zirconium oxide was placed in a porcelain crucible and calcined at 400° C. for 3 hours in air using an electric furnace and pulverized in an agate mortar to obtain powdery zirconium oxide (hereinafter referred to as "carrier A"). The BET specific surface area of carrier A, which was measured by a nitrogen adsorption method, was 102.7 m²/g.

Catalyst Preparation Example 1

A catalyst containing palladium as a specific metal component was prepared by the following method.

To carrier A (5.0 g), an aqueous solution containing 0.66 wt % palladium chloride and 0.44 wt % sodium chloride was added to allow the metal component to adsorb onto the carrier. To this, an aqueous formaldehyde-sodium hydroxide solution was poured to quickly reduce the adsorbed metal component. Then, the resultant catalyst was washed with ion-exchange water and dried to prepare a zirconium oxide catalyst carrying 1.0 wt % palladium (hereinafter referred to as "A1 catalyst").

The hydrogenation reduction reaction was carried out by the following method.

Example 1

In a 100-mL SUS reactor, A1 catalyst (0.60 g), compound A (1.8 g) and normal hexane (24.6 g) were placed and the reactor was purged with nitrogen gas. Thereafter, the reactor was charged with hydrogen gas up to 8.5 MPa. The temperature was increased to a reaction temperature of 230° C. and the reaction was performed for 5 hours. Thereafter, the reactor was cooled and the content thereof was collected and analyzed by gas chromatography. As a result, the conversion of compound A was 100% and the selectivity to a product, 1,4-bis(3-hydroxy-2,2-dimethylpropoxy)cyclohexane (total of geometric isomers), was 85.5%. At the time, the geometric isomer ratio (cis/trans ratio) of the product was 61.0/39.0. The reaction scheme in Example 1 is shown below.

Hydrogenation reduction reaction of polycyclic acetal of Example 1.

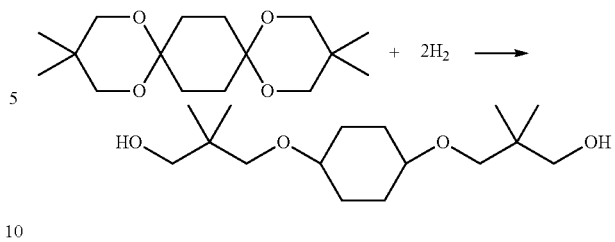

The product was isolated by chromatography and the structure was checked by NMR analysis.

(cis-form) colorless, oily
$^1$H NMR (500 MHz, $CDCl_3$)
δ 0.92 (6H×2, s×2, $C\underline{H}_3C×4$), 1.53-1.60 (4H, m, c-Hexane($\underline{H}_{ax}$)), 1.68-1.78 (4H, m, c-Hexane($\underline{H}_{eq}$)), 2.96 (2H, t, —O$\underline{H}$), 3.29 (4H, s, —C($CH_3$)$_2$$C\underline{H}_2$O-×2), 3.29-3.33 (2H, m, —OC$\underline{H}$($CH_2$)$_2$-×2), 3.46 (4H, d, $C\underline{H}_2$OH).

$^{13}$C NMR (125 MHz, $CDCl_3$)
δ 21.9, 27.3, 35.9, 72.4, 75.8, 77.9.

(trans-form) white, solid
$^1$H NMR (500 MHz, $CDCl_3$)
δ 0.92 (6H×2, s×2, $C\underline{H}_3C×4$), 1.32-1.41 (4H, m, c-Hexane($\underline{H}_{ax}$)), 1.85-1.95 (4H, m, e-Hexane($\underline{H}_{eq}$)), 3.03 (2H, t, —O$\underline{H}$), 3.25-3.33 (2H, m, —OC$\underline{H}$($CH_2$)$_2$-×2), 3.31 (4H, s, —C($CH_3$)$_2$$C\underline{H}_2$O-×2), 3.45 (4H, d, $C\underline{H}_2$OH).

$^{13}$C NMR (125 MHz, $CDCl_3$)
δ 21.9, 27.8, 35.9, 72.6, 76.7, 78.5.

Example 2

In a 100-mL SUS reactor, A1 catalyst (0.60 g), compound A (1.8 g) and diisopropyl ether (24.3 g) were placed. The reaction was performed in the same manner as in Example 1 at a reaction temperature of 230° C. for 3 hours. As a result, the conversionof compound A was 100% and the selectivity to a product, 1,4-bis(3-hydroxy-2,2-dimethylpropoxy)cyclohexane (total of geometric isomers), was 87.6%. At the time, the geometric isomer ratio (cis/trans ratio) of the product was 61.9/38.1.

Example 3

In a 100-mL SUS reactor, A1 catalyst (0.80 g), compound A (5.0 g) and 1,4-dioxane (24.2 g) were placed. The reaction was performed in the same manner as in Example 1 at a reaction temperature of 230° C. for 3 hours. As a result, the conversion of compound A was 100% and the selectivity to a product, 1,4-bis(3-hydroxy-2,2-dimethylpropoxy)cyclohexane (total of geometric isomers), was 93.3%. At the time, the geometric isomer ratio (cis/trans ratio) of the product was 67.4/32.6.

Example 4

In a 100-mL SUS reactor, Al catalyst (0.80 g), compound B (6.5 g) and 1,4-dioxane (24.4 g) were placed. The reaction was performed in the same manner as in Example 1 at a reaction temperature of 230° C. for 3 hours. As a result, the conversion of compound B was 100% and the selectivity to a product, 1,4-bis(3-hydroxy-2,2-diethylpropoxy)cyclohexane (total of geometric isomers), was 88.3%. At the time, the geometric isomer ratio (cis/trans ratio) of the product was 70.9/29.1. The reaction scheme in Example 4 is shown below.

Hydrogenation reduction reaction of polycyclic acetal of Example 4.

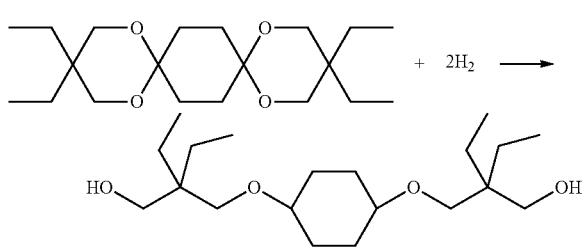

The product was isolated by chromatography and the structure was checked by NMR analysis.

(cis-form) colorless, oily

¹H NMR (500 MHz, CDCl₃)

δ 0.81 (t, —CH₂C$\underline{H}$₃, 12H), 1.26-1.41 (m, —C$\underline{H}$₂CH₃, 8H), 1.54-1.59 (m, c-Hexane ($\underline{H}_{ax}$), 4H), 1.68-1.74 (m, c-Hexane($\underline{H}_{eq}$), 4H), 3.06 (t, —O$\underline{H}$, 2H), 3.29 (m, —OC$\underline{H}$(CH₂)₂—, 2H), 3.34 (s, —C(C₂H₅)₂C$\underline{H}$₂O—, 4H), 3.51 (d, C$\underline{H}$₂OH, 4H).

¹³C NMR (125 MHz, CDCl₃)

δ 7.83, 22.98, 27.37, 40.46, 69.33, 75.39, 77.22.

(trans-form) white, solid

¹H NMR (500 MHz, CDCl₃)

δ 0.81 (t, —CH₂C$\underline{H}$₃, 12H), 1.26-1.58 (m, —C$\underline{H}$₂CH₃ & c-Hexane ($\underline{H}_{ax}$), 12H), 1.89-1.91 (m, c-Hexane($\underline{H}_{eq}$), 4H), 3.13 (t, —O$\underline{H}$, 2H), 3.29 (m, —OC$\underline{H}$(CH₂)₂—, 2H), 3.37 (s, —C(C₂H₅)₂C$\underline{H}$₂O—, 4H), 3.50 (d, C$\underline{H}$₂OH, 4H).

¹³C NMR (125 MHz, CDCl₃)

δ 7.38, 22.97, 27.78, 40.44, 69.55, 75.90, 77.22.

Example 5

In a 100-mL SUS reactor, A1 catalyst (0.80 g), compound C (6.6 g) and 1,4-dioxane (24.4 g) were placed. The reaction was performed in the same manner as in Example 1 at a reaction temperature of 230° C. for 3 hours. As a result, the conversion of compound C was 100% and the selectivity to a product, 1,4-bis(3-hydroxy-2-methyl-2-propylpropoxy)cyclohexane (total of geometric isomers), was 89.5%. At the time, the geometric isomer ratio (cis/trans ratio) of the product was 70.6/29.4. The reaction scheme in Example 5 is shown below.

Hydrogenation reduction reaction of polycyclic acetal of Example 5.

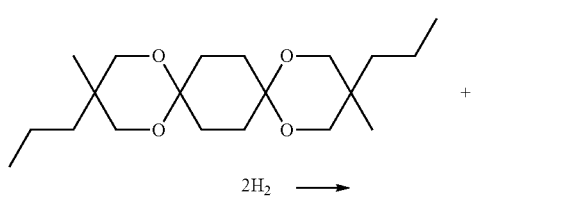

The product was isolated by chromatography and the structure was checked by NMR analysis.

(cis-form) colorless, oily

¹H NMR (500 MHz, CDCl₃)

δ 0.83 (s, —C$\underline{H}$₃, 6H), 0.92 (t, —(CH₂)₂C$\underline{H}$₃, 6H), 1.24-1.34 (m, —(C$\underline{H}$₂)₂CH₃, 8H), 1.54-1.58 (m, c-Hexane ($\underline{H}_{ax}$), 4H), 1.70 (m, c-Hexane($\underline{H}_{eq}$), 4H), 3.12 (t, —O$\underline{H}$, 2H), 3.27-3.35 (m, —OC$\underline{H}$(CH₂)₂ & —C(CH₃)(C₃H₇)C$\underline{H}$₂O—, 6H), 3.48 (d, C$\underline{H}$₂OH, 4H).

¹³C NMR (125 MHz, CDCl₃)

δ 14.94, 16.51, 18.93, 27.17, 27.31, 36.85, 38.29, 71.06, 75.75, 76.81.

(trans-form) colorless, oily

¹H NMR (500 MHz, CDCl₃)

δ 0.82 (s, —C$\underline{H}$₃, 6H), 0.91 (t, —(CH₂)₂C$\underline{H}$₃, 6H), 1.27-1.31 (m, —(C$\underline{H}$₂)₂CH₃, 8H), 1.33-1.38 (m, c-Hexane ($\underline{H}_{ax}$), 4H), 1.89-1.91 (m, c-Hexane($\underline{H}_{eq}$), 4H), 3.21 (s, —O$\underline{H}$, 2H), 3.29-3.36 (m, —OC$\underline{H}$(CH₂)₂ & C(CH₃)(C₃H₇)C$\underline{H}$₂O—, 6H), 3.46 (s, C$\underline{H}$₂OH, 4H).

¹³C NMR (125 MHz, CDCl₃)

δ 14.91, 16.46, 18.85, 27.66, 27.75, 36.79, 38.26, 71.03, 76.75, 77.12.

Example 6

In a 100-mL SUS reactor, A1 catalyst (0.80 g), compound D (6.2 g) and 1,4-dioxane (24.7 g) were placed. The reaction was performed in the same manner as in Example 1 at a reaction temperature of 230° C. for 3 hours. As a result, the conversion of compound D was 100% and the selectivity to a product, 1,4-bis(3-hydroxy-2-butyl-2-ethylpropoxy)cyclohexane (total of geometric isomers), was 75.6%. At the time, the geometric isomer ratio (cis/trans ratio) of the product was 72.5/27.5. The reaction scheme in Example 6 is shown below.

Hydrogenation Reduction Reaction of Polycyclic Acetal of Example 6

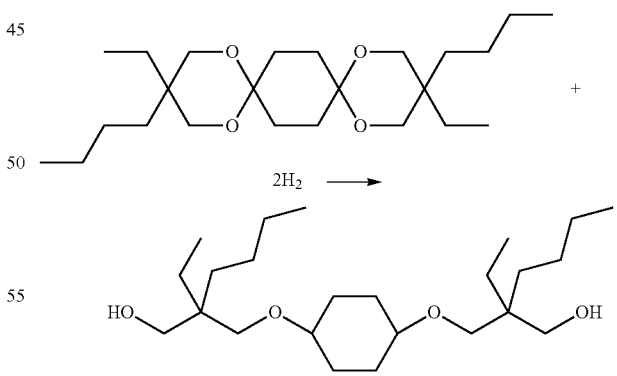

The product was isolated by chromatography and the structure was checked by NMR analysis.

(cis-form) colorless, oily

¹H NMR (500 MHz, CDCl₃)

δ 0.81 (t, —CH₂C$\underline{H}$₃, 6H), 0.90 (t, —CH₂C$\underline{H}$₃, 6H), 1.12-1.43 (m, —C$\underline{H}$₂CH₃ & (C$\underline{H}$₂)₃CH₃ 16H), 1.53-1.60 (m, c-Hexane($\underline{H}_{ax}$), 4H), 1.68-1.74 (m, c-Hexane($\underline{H}_{eq}$), 4H), 3.07

(t, —O<u>H</u>, 2H), 3.28-3.32 (m, —OC<u>H</u>(CH$_2$)$_2$, 2H), 3.34 (s, C(C$_2$H$_5$)(C$_4$H$_9$)C<u>H</u>$_2$O—, 4H), 3.51 (d, —C<u>H</u>$_2$OH, 4H).

$^{13}$C NMR (125 MHz, CDCl$_3$)

δ 7.47, 14.12, 23.53, 23.63, 25.11, 27.34, 27.39, 40.62, 69.64, 75.63, 75.88.

(trans-form) colorless, oily $^1$H NMR (500 MHz, CDCl$_3$)

δ 0.81 (t, —CH$_2$C<u>H</u>$_3$, 6H), 0.90 (t, —CH$_2$C<u>H</u>$_3$, 6H), 1.11-1.42 (m, —C<u>H</u>$_2$CH$_3$ & —(C<u>H</u>$_2$)$_3$CH$_3$ & c-Hexane (<u>H</u>$_{ax}$), 20H), 1.90 (br-d, c-Hexane(<u>H</u>$_{eq}$), 4H), 3.13 (t, —O<u>H</u>, 2H), 3.26-3.31 (m, —OC<u>H</u>(CH$_2$)$_2$, 2H), 3.37 (s, C(C$_2$H$_5$)(C$_4$H$_9$)C<u>H</u>$_2$O—, 4H), 3.50 (br-d, C<u>H</u>$_2$OH, 4H).

$^{13}$C NMR (125 MHz, CDCl$_3$)

δ 7.48, 14.11, 23.53, 23.63, 25.11, 27.78, 27.80, 30.47, 40.44, 69.89, 76.22.

Comparative Example 1

In a 100-mL SUS reactor, A1 catalyst (0.60 g), compound E (1.5 g) and normal hexane (24.9 g) were placed. The reaction was performed in the same manner as in Example 1 at a reaction temperature of 230° C. for 3 hours. As a result, the conversion of compound E was 100% and the selectivity to a product, 1,4-bis(3-hydroxypropoxy)cyclohexane (total of geometric isomers), was 24.2%. The reaction scheme in Comparative Example 1 is shown below.

Hydrogenation Reduction Reaction of Polycyclic Acetal of Comparative Example 1

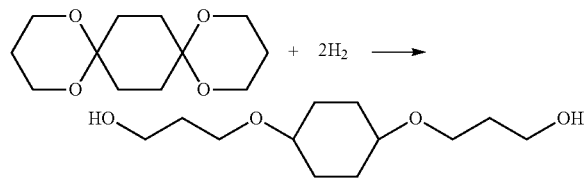

Comparative Example 2

In a 100-mL SUS reactor, A1 catalyst (0.60 g), compound E (1.5 g) and 1,4-dioxane (24.3 g) were placed. The reaction was performed in the same manner as in Example 1 at a reaction temperature of 210° C. for 5 hours. As a result, the conversion of compound E was 95.9% and the selectivity to a product, 1,4-bis(3-hydroxypropoxy)cyclohexane (total of geometric isomers), was 46.5%.

Comparative Example 3

In a 100-mL SUS reactor, A1 catalyst (0.60 g), 1,4-cyclohexanedione-bis(ethylene ketal) (a reagent, manufactured by Tokyo Kasei Kogyo Co., Ltd.) (1.2 g) and normal hexane (24.8 g) were placed. The reaction was performed in the same manner as in Example 1 at a reaction temperature of 210° C. for 3 hours. As a result, the conversion of 1,4-cyclohexanedione-bis(ethylene ketal) was 99.7%. The product, 1,4-bis(2-hydroxyethoxy)cyclohexane, was produced in a trace amount; at the same time, many decomposition by-products were found. Note that, 1,4-cyclohexanedione-bis(ethylene ketal) is a compound represented by the following formula.

Comparative Example 4

In a 100-mL SUS reactor, A1 catalyst (0.60 g), 1,4-cyclohexanedione-bis(ethylene ketal) (a reagent, manufactured by Tokyo Kasei Kogyo Co., Ltd.) (1.3 g) and diisopropyl ether (25.2 g) were placed. The reaction was performed in the same manner as in Example 1 at a reaction temperature of 210° C. for 3 hours. As a result, the conversion of 1,4-cyclohexanedione-bis(ethylene ketal) was 88.9%. The product, 1,4-bis(2-hydroxyethoxy)cyclohexane, was obtained in a trace amount; at the same time, many decomposition by-products were found.

(Physical Property Evaluation of Compound)

As an index for lipophilicity of a chemical substance, 1-octanol/water partition coefficient is known. The partition coefficient can be obtained by the methods specified in Japanese Industrial Standards Z7260-107 (2000) and OECD Guidelines for the Testing of Chemicals 107. Generally, a large partition coefficient value (logP$_{ow}$ value) means that the material is lipophilic. It is known that the value can be obtained not only by actual measurement but also by estimation from the molecular structure of a compound. The United States Environmental Protection Agency gives out calculation software under the name of "The Estimations Programs Interface for Windows" developed for the purpose of evaluating environmental effects of chemical substances. Using one of the software modules, "KOWWIN version 1.68 (2010.09)", the partition coefficients of the above substances were estimated.

Known compounds known in the art analogous to the compound of the present invention, namely, 1,4-bis(2-hydroxyethoxy)cyclohexane and 1,4-bis(3-hydroxypropoxy)cyclohexane, which were synthesized in the above Comparative Examples, and the representative compounds of the present invention, namely, 1,4-bis(3-hydroxy-2,2-dimethylpropoxy)cyclohexane, 1,4-bis(3-hydroxy-2,2-diethylpropoxy)cyclohexane, 1,4-bis(3-hydroxy-2-methyl-2-propylpropoxy)cyclohexane and 1,4-bis(3-hydroxy-2-butyl-2-ethylpropoxy)cyclohexane, which were synthesized in the above Examples, were evaluated for lipophilicity.

1,4-Bis(2-hydroxyethoxy)cyclohexane and 1,4-bis(3-hydroxypropoxy)cyclohexane were expressed by the "smiles" notation based on the chemical structures, as "OCCOC(C1)CCC(C1)OCCO" and "OCCCOC(C1)CCC(C1)OCCCO", respectively, and input into a computer to obtain distribution coefficient values of −0.04 and 0.94, respectively. Also, with respect to 1,4-bis(3-hydroxy-2,2-dimethylpropoxy)cyclohexane, 1,4-bis(3-hydroxy-2,2-diethylpropoxy)cyclohexane, 1,4-bis(3-hydroxy-2-methyl-2-propylpropoxy)cyclohexane and 1,4-bis(3-hydroxy-2-butyl-2-ethylpropoxy)cyclohexane, the notations: "CC(CO)(COC(C1)CCC(C1)OCC(CO) (C)C)C", "CCC(CO) (COC(C1)CCC(C1)OCC(CO) (CC)CC)CC", "CCCC(C0)(C)COC(C1)CCC(C1)OCC(CO)(C)CCC", and "CCC(CO)(COC(C1)CCC(C1)OCC(CO)(CC)CCCC)CCCC" were input into a computer to obtain distribution coefficient values of 2.68, 4.65, 4.65 and 6.61, respectively. From these estimation results, it was considered that the compound of the present invention is more lipophilic.

The distribution coefficients were also estimated by inputting the above smiles strings into Y-MB method estimation module (parameter set 2014n is used) installed in commercially available software "HSPiP version 4.1.07", which is a physical property estimation program of Hansen solubility parameter. As a result, the distribution coefficient of 1,4-bis (2-hydroxyethoxy)cyclohexane was −0.557, the distribution coefficient of 1,4-bis(3-hydroxypropoxy)cyclohexane was 0.889. The distribution coefficient of 1,4-bis(3-hydroxy-2,2-dimethylpropoxy)cyclohexane was 3.16. The distribution coefficient of 1,4-bis(3-hydroxy-2,2-diethylpropoxy)cyclohexane was 4.65. The distribution coefficient of 1,4-bis(3-hydroxy-2-methyl-2-propylpropoxy)cyclohexane was 4.71. The distribution coefficient of 1,4-bis(3-hydroxy-2-butyl-2-ethylpropoxy)cyclohexane was 6.94.

The estimated values differ in absolute value between the two software tools; however, the values show the same tendency, that is, the compound of the present invention is more lipophilic than the analogous compounds known in the art.

The present application is based on a Japanese Patent Application filed on Sep. 29, 2014 (Application No. 2014-198480), the content of which is incorporated herein by reference.

INDUSTRIAL APPLICABILITY

The novel polyether diol according to the present invention composed of a cyclohexane ring structure and a neopentyl glycol structure can be suitably used as a raw material for manufacturing a resin having not only high lipophilicity but also excellent thermal stability. Such a polyether diol can be efficiently produced by hydrogenation reduction of a polycyclic acetal compound in the presence of a hydrogenation catalyst.

The invention claimed is:

1. A polyether diol compound of formula (3):

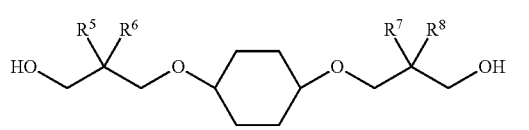

(3)

wherein $R^5$, $R^6$, $R^7$ and $R^8$, which may be the same as or different from each other, each represent a linear or branched alkyl group having 1 to 6 carbon atoms.

2. The compound according to claim 1, wherein a combination of $R^5$ and $R^6$ and a combination of $R^7$ and $R^8$ are the same as each other.

3. The compound according to claim 1, wherein at least one of the combination of $R^5$ and $R^6$ and the combination of $R^7$ and $R^8$ is a combination of substituent groups selected from the group consisting of a combination of a methyl group and a methyl group, a combination of an ethyl group and an ethyl group, a combination of a methyl group and a normal propyl group, and a combination of an ethyl group and a normal butyl group.

4. The compound according to claim 1, wherein all of $R^5$, $R^6$, $R^7$ and $R^8$ are a methyl group.

5. A method for producing a polyether diol, comprising: performing hydrogenation reduction of a compound of formula (1) in the presence of a hydrogenation catalyst to obtain a polyether diol compound of formula (2):

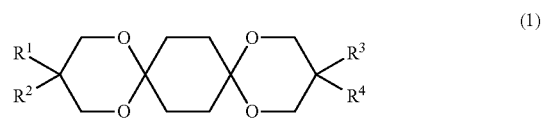

(1)

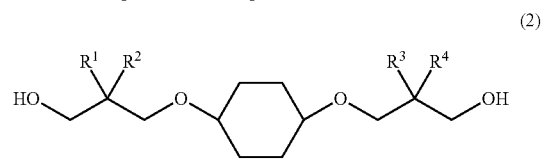

(2)

wherein $R^1$, $R^2$, $R^3$ and $R^4$, which may be the same as or different from each other, each represent a linear or branched alkyl group having 1 to 6 carbon atoms.

6. The production method according to claim 5, wherein a combination of $R^1$ and $R^2$ and a combination of $R^3$ and $R^4$ are the same as each other.

7. The production method according to claim 5, wherein at least one of the combination of $R^1$ and $R^2$ and the combination of $R^3$ and $R^4$ is a combination of substituent groups selected from the group consisting of a combination of a methyl group and a methyl group, a combination of an ethyl group and an ethyl group, a combination of a methyl group and a normal propyl group, and a combination of an ethyl group and a normal butyl group.

8. The production method according to claim 5, wherein all of $R^1$, $R^2$, $R^3$ and $R^4$ are a methyl group.

9. The production method according to claim 5, wherein the compound of formula (1) is subjected to hydrogenation reduction in a reaction solvent comprising at least one selected from the group consisting of ether compounds and saturated hydrocarbon compounds.

10. The production method according to claim 5, wherein the hydrogenation catalyst is a solid catalyst comprising palladium.

11. The production method according to claim 5, wherein the hydrogenation catalyst is a solid catalyst comprising a zirconium compound.

12. The method according to claim 6, wherein the compound of formula (1) is subjected to hydrogenation reduction in a reaction solvent comprising at least one selected from the group consisting of ether compounds and saturated hydrocarbon compounds.

13. The method according to claim 6, wherein the hydrogenation catalyst is a solid catalyst comprising palladium.

14. The method according to claim 6, wherein the hydrogenation catalyst is a solid catalyst comprising a zirconium compound.

15. The method according to claim 7, wherein the compound of formula (1) is subjected to hydrogenation reduction in a reaction solvent comprising at least one selected from the group consisting of ether compounds and saturated hydrocarbon compounds.

16. The method according to claim 7, wherein the hydrogenation catalyst is a solid catalyst comprising palladium.

17. The method according to claim 7, wherein the hydrogenation catalyst is a solid catalyst comprising a zirconium compound.

18. The method according to claim 8, wherein the compound of formula (1) is subjected to hydrogenation reduction in a reaction solvent comprising at least one selected from the group consisting of ether compounds and saturated hydrocarbon compounds.

19. The method according to claim 8, wherein the hydrogenation catalyst is a solid catalyst comprising palladium.

20. The method according to claim 8, wherein the hydrogenation catalyst is a solid catalyst comprising a zirconium compound.

\* \* \* \* \*